(12) United States Patent
Tang

(10) Patent No.: US 10,071,157 B2
(45) Date of Patent: *Sep. 11, 2018

(54) METHOD OF INDUCING TOLERANCE TO AN ALLERGEN

(71) Applicant: MURDOCH CHILDRENS RESEARCH INSTITUTE, Parkville VIC (AU)

(72) Inventor: Mimi Lai-Kuan Tang, Malvern (AU)

(73) Assignee: MURDOCH CHILDRENS RESEARCH INSTITUTE, Parkville VIC (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/098,428

(22) Filed: Apr. 14, 2016

(65) Prior Publication Data
US 2016/0228542 A1 Aug. 11, 2016

Related U.S. Application Data

(63) Continuation of application No. 12/865,499, filed as application No. PCT/AU2009/000104 on Jan. 30, 2009, now Pat. No. 9,402,896.

(30) Foreign Application Priority Data

Feb. 1, 2008 (AU) ................. 2008900463

(51) Int. Cl.
| | | |
|---|---|---|
| *A01N 63/00* | (2006.01) | |
| *A01N 65/00* | (2009.01) | |
| *A61K 39/35* | (2006.01) | |
| *A61K 39/36* | (2006.01) | |
| *A61K 39/39* | (2006.01) | |
| *A61K 39/00* | (2006.01) | |

(52) U.S. Cl.
CPC ............. *A61K 39/39* (2013.01); *A61K 39/35* (2013.01); *A61K 2039/52* (2013.01); *A61K 2039/523* (2013.01); *A61K 2039/55* (2013.01); *A61K 2039/552* (2013.01); *A61K 2039/55594* (2013.01); *A61K 2039/577* (2013.01)

(58) Field of Classification Search
None
See application file for complete search history.

(56) References Cited

U.S. PATENT DOCUMENTS

| | | |
|---|---|---|
| 6,506,380 B1 | 1/2003 | Isolauri et al. |
| 7,060,687 B2 | 6/2006 | Hsu et al. |
| 9,402,896 B2 * | 8/2016 | Tang ............ A61K 39/35 |
| 2005/0180961 A1 | 8/2005 | Pecquet et al. |
| 2006/0233772 A1 | 10/2006 | Herz et al. |
| 2008/0233155 A1 | 9/2008 | Moingeon et al. |
| 2008/0254058 A1 | 10/2008 | Glenting et al. |
| 2009/0169582 A1 | 7/2009 | Chua et al. |
| 2009/0297564 A1 | 12/2009 | Hernandez et al. |
| 2011/0097361 A1 | 4/2011 | Tang |

FOREIGN PATENT DOCUMENTS

| | | |
|---|---|---|
| EP | 1 364 586 A1 | 11/2003 |
| EP | 1 723 965 A1 | 11/2006 |
| EP | 2244734 | 5/2016 |
| WO | 01/37865 A1 | 5/2001 |
| WO | 01/66136 A2 | 9/2001 |
| WO | 03/099037 A1 | 12/2003 |
| WO | 2006/123230 A2 | 11/2006 |

OTHER PUBLICATIONS

Hsiao et al. 'Long-term clinical and immunological effects of probiotic and peanut oral immunotherapy after treatment cessation: 4-year follow-up of a randomised, double-blind, placebo-controlled trial.'Lancet Child Adolesc Heal;th 1:97-105, 2017.*
International Search Report and Written Opinion corresponding to PCT/AU2009/000104, dated Feb. 25, 2009, 7 pages.
Supplementary European Search Report corresponding to EP 09706855, dated Apr. 19, 2012, 6 pages.
Almeida et al., "Microbial population present in fermented beverage cauim produced by Brazilian Amerindians," Int. J. Food Microbiol., 2007, 120:146-151.
Attwood et al., "The Babel of Bioinformatics," Science, 2000, 290(5491):471-473.
Blumenthal et al., in Allergens and Allergen Immunotherapy, 3$^{rd}$ edition, 2004, pp. 37-51.
Buchanan et al., "Egg oral immunotherapy in nonanaphylactic children with egg allergy," J. Allergy Clin. Immunol., 2007, vol. 119:199-205.
Bucker et al., "Lactic Fermentation of Peanut Milk," J. Food Science, 1979, 44(5):1534-1538.
Colonna et al., "Plasmacytoid dendritic cells in immunity," Nature Immunology, Dec. 2004, vol. 5(12), pp. 1219-1226.
Glenting et al., "Production of Recombinant Peanut Allergen Ara h 2 using Lactococcus lactis," 2007, 66(28):1-10.
Isolauri et al., "Probiotics in the management of atopic eczema," Clin Exp Allergy, 2000, 30(11):1604-10 (Pubmed Abstract).
Justicia et al., "Higher evidence for specific immunotherapy than reported in the ARIA update," J. Allergy Clin. Immunol., Feb. 2008, p. 536 (Addendum to J. Allergy Clin. Immunol., 2007, vol. 119).
Lee et al., "Selection of Anti-Allergic Lactobacillus in Murine Model of Peanut Allergy," Pediatric Allergy and Respiratory Disease, 2007, vol. 17, No. 3, pp. 260-270.

(Continued)

*Primary Examiner* — Nora Rooney
(74) *Attorney, Agent, or Firm* — Mintz Levin Cohn Ferris Glovsky and Popeo PC

(57) ABSTRACT

The present invention relates generally to the field of allergies. More particularly, the present invention provides a method for treating an allergy in a subject by inducing tolerance to an allergen associated with the allergy. Medicinal kits useful in protocols to induce tolerance or reduce intolerance in a subject also form part of the present invention.

4 Claims, No Drawings

(56) References Cited

OTHER PUBLICATIONS

Majamaa et al., "Probiotics: A novel approach in the management of food allergy," Journal of Allergy and Clinical Immunology, 1997, 99:179-185.
Matsuzaki et al., "Modulating immune responses with probiotic bacteria," Immunology and Cell Biology, 2000, 78:67-73.
Menard et al., "Stimulation of Immunity Without Alteration of Oral Tolerance in Mice Fed with Heat-Treated Fermented Infant Formula," Journal of Pediatric Gastroenterology & Nutrition, 2006, 43:451-458.
Nelson et al., "Treatment of anaphylactic sensitivity to peanuts by immunotherapy with injections of acqueous peanut extract," J. Allergy Clin. Immunol., 1997, vol. 99:744-751.
Ngo et al., "Computational Complexity, Protein Structure Prediction, and the Levinthal Pardox," The Protein Folding Problem and Tertiary Structure Prediction, Ed. K. Merz and S. Le Grand. Boston: Birkhauser, 1994, 491-495.
Nials et al., "Mouse models of allergic asthma: acute and chronic allergen challenge," Disease Models & Mechanisms, 2008, vol. 1, pp. 213-220.
Pan et al., "Comparison of Efficacy of a Novel Probiotic from Koji Fermentation (ImmuSoy) with LGG on Peanut Alelrgy," Journal of Allergy and Clinical Immunology, 2006, 117:s327 (Abstract).
Passalacqua et al., "Allergic Rhinitis and its Impact on Asthma update: Allergen immunotherapy," J. Allergy Clin. Immunol., 2007, vol. 119, pp. 881-891.
Schaffner et al., "Fermentation of aqueous plant seed extracts by lactic acid bacteria," Appl. Environ. Microbiol., 1986, 51(5):1072-1076.
Skolnick et al., "From genes to protein structure and function: novel applications of computational approaches in the genomic era," Trends in Biotech, 2000, 18:34-39.
Staden et al., "Specific oral tolerance induction in food allergy in children: efficacy and clinical patterns of reaction," Allergy, 2007, vol. 62:1261-1269.
Tang et al., "Administration of a probiotic with peanut oral immunotherapy: A randomized trial,"J. Allergy Clin. Immunol., Mar. 2015, vol. 135, pp. 737-744.
Extended European Search Report corresponding to EP 16167496.5, dated Oct. 13, 2016, 10 pages.
Bruzzese, E. et al., "Impact of prebiotics on human health," *Digestive and Liver Disease* (Dec. 1, 2006) 38(2):S283-S287.
Kukkonen, Kaarina et al., "Probiotics and prebiotic galacto-oligosaccharides in the prevention of allergic diseases: A randomized, double-blind, placebo-controlled trial," *J. Allergy Clin. Immunol.* (Jan. 1, 2007); 119:192-198.
Moro, G. et al., "A mixture of prebiotic oligosaccharides reduces the incidence of atopic dermatitis during the first six months of age," *Arch Dis Child* (Jul. 27, 2006); 91:814-819.
Notice of Opposition corresponding to EP2244734 in the name of Murdoch Childrens Research Institute filed on behalf of N.V. Nutricia dated Dec. 14, 2016; 10 pages.
Notice of Opposition corresponding to EP2244734 in the name of Murdoch Childrens Research Institute filed on behalf of Nestec S.A. dated Feb. 3, 2017; 15 pages.
Chin, James et al., "Immune response to orally consumed antigens and probiotic bacteria," *Immunology and Cell Biology* (2000; accepted Sep 13, 1999); 78:55-66.
Ciprandi, G. et al., "*Bacillus clausii* effects in children with allergic rhinitis," *Allergy* (2005; accepted Jul. 27, 2004); 2 pages.
Ishida, Yu et al., "Effect of Milk Fermented with *Lactobacillus acidophilus* Strain L-92 on Symptoms of Japanese Cedar Pollen Allergy: A Randomized Placebo-Controlled Trial," *Biosci. Biotechnol. Biochem.* (May 1, 2005); 69(9)1652-1660.
Prioult, Guénolée et al., "Effect of Probiotic Bacteria on Induction and Maintenance of Oral Tolerance to β-Lactodlobulin in Gnotobiotic Mice," *Clinical and Diagnostic Laboratory Immunology* (Sep. 2003; accepted May 22, 2003); 10(5):787-792.
Repa, Andreas et al., "Mucosal co-application of lactic add bacteria and allergen induces counter-regulatory immune responses in a murine model of birch pollen allergy," *Vaccine* (Jul. 3, 2003); 22:87-95.
Belz, G., The Belz Declaration (first) in European Patent No. 2244734, Jul. 21, 2017, Melbourne Australia, 38 pages.
Colonna, M. et al., "Plasmacytoid Dendritic Cells in Immunity," Nature Immunology, Dec. 2004, pp. 1219-1226, vol. 5, No. 12, © Nature Publishing Group, 8 pages.
Goubier, A., et al., "Plasmacytoid Dendritic Cells Mediate Oral Tolerance," Immunity, Sep. 19, 2008, pp. 464-475, vol. 19, © Elsevier Inc., 12 pages.
Steinman, R. M. et al., "Tolerogenic Dendritic Cells," Annual Review of Immunology, 2003, pp. 685-711, vol. 21, © Annual Reviews, 30 pages.
Nash, S. D. et al, "Oral Peanut Immunotherapy for Peanut Allergic Patients," The Journal of Allergy and Clinical Immunology, Jan. 2007, S158 Abstracts, No. 622, 1 page.
Scurlock, A. M. et al., "Safety Oral Peanut Immunotherapy for Peanut Allergic Patients," The Journal of Allergy and Clinical Immunology, Feb. 2005, S246 Abstracts, No. 979, 1 page.
Patriarca, G. et al., "Oral Desensitizing Treatment in Food Allergy: Clinical and Immunological Results," Alimentary Pharmacology & Therapeutics, 2003, pp. 459-465, vol. 17, © Blackwell Publishing Ltd., 7 pages.
Salminen, S. J., The Salminen Declaration in European Patent No. 2244734, Jul. 20, 2017, Turku Finland, 9 pages.
Kohler, H. et al., "Bacterial-Enterocyte Crosstalk: Cellular Mechanisms in Health and Disease," Journal of Pediatric Gastroenterology and Nutrition, Feb. 2003, pp. 175-185, vol. 36, © Lippincott Williams & Wilkins, Inc. Philadelphia, 11 pages.
Servin, A.L. and Coconnier, M. H., "Adhesion of Probiotic Strains to the Intestinal Mucosa and Interaction with Pathogens," Best Practice & Research Clinical Gastroenterology, 2003, pp. 741-754, vol. 17, No. 5, © Elsevier Ltd., 14 pages.
Strentebjerg-Olesen, B. et al., "Type 1 Fimbriation and Phase Switching in a Natural *Escherichia coli* fimB Null Strain, Nissle 1917," Journal of Bacteriology, Dec. 1999, pp. 7470-7478, vol. 181, No. 24, © American Society for Microbiology, 9 pages.
Vinderola, C. G., The Vinderola Declaration in European Patent No. 2244734, Jul. 24, 2017, Santa Fe Argentina, 12 pages.
Smith, K. M. et al., "Oral Tolerance," American Journal of Respiratory and Critical Care Medicine, 2000, pp. S175-S178, vol. 162, University of Glasgow, Glasgow United Kingdom, 4 pages.
Mowat, A. M. et al., "Oral Tolerance: Overview and Historical Perspectives," Annals of the New York Academy of Sciences, 2004, pp. 1-8, vol. 1029, © New York Academy of Sciences, 8 pages.
Perez-Machado, M. A. et al., "Reduced Transforming Growth Factor-β1-producing T Cells in the Duodenal Mucosa of Children with Food Allergy," European Journal of Immunology, 2003, pp. 2307-2315, No. 33, © Wiley-VCH Verlag GmbH & Co. KGaA, Weinheim, 9 pages.
Karlsson, M. R. et al. "Allergen-Responsive CD4$^+$ CD25$^+$ Regulatory T Cells in Children Who Have Outgrown Cow's Milk Allergy," Journal of Experimental Medicine, Jun. 21, 2004, pp. 1679-1688, vol. 199, No. 12, © The Rockefeller University Press, 10 pages.
Yazdanbakhsh, M. et al., "Allergy, Parasites, and the Hygiene Hypothesis," Science's Compass: Review: Immunology, Apr. 19, 2002, pp. 490-494, vol. 296 (5567), © American Association for the Advancement of Science, 12 pages.
Rautava, S. et al., "Probiotics During Pregnancy and Breast-Feeding Might Confer Immunomodulatory Protection Against Atopic Disease in the Infant," The Journal of Allergy and Clinical Immunology, 2002, pp. 119-121, vol. 109, No. 1, © Mosby, Inc., 3 pages.
Prescott, S. L. et al., "Supplementation with *Lactobacillus rhamnosus* or *Bifidobacterium lactis* Probiotics in Pregnancy Increases Cord Blood Interferon-$\gamma$ and Breast Milk Transforming Growth Factor-β and Immunoglobin A Detection," Clinical and Experimental Allergy, 2008, pp. 1606-1614, vol. 38, © The Authors, © Blackwell Publishing Ltd., 9 pages.

(56) References Cited

OTHER PUBLICATIONS

Pessi, T. et al "Interleukin-10 Generation in Atopic Children Following Oral *Lactobacillus rhamnosus* GG," Clinical and Experimental Allergy, 200, pp. 1804-1808, vol. 30, © Blackwell Science Ltd., 5 pages.
Foligne, B. et al., "Correlation Between in vitro and in vivo Immunomodulatory Properties of Lactic Acid Bacteria," World Journal of Gastroeuterology, 2007, pp. 236-243, vol. 13 (2), © The WJG Press, 8 pages.
Medina, B. et al., "Differential Immunomodulatory Propertyies of *Bifidobacterium logum* Strains: Relevance to Probiotic Selection and Clinical Applications," Clinical and Experimental Immunology, pp. 531-538, vol. 150, © Consejo Superior de Investigaciones Cientifices © British Society for Immunology, 8 pages.
Maassen, B. M. et al., "Strain-Dependent Induction of Cytokine Profiles in the Gut by Orally Administered Lactobacillus Strains," Vaccine Journal, 2000, pp. 2613-2623, vol. 18, © Elsevier Science Ltd., 11 pages.
Von Der Weid, T. et al., "Induction by a Lactic Acid Bacterium of a Population of CD4+ T Cells with Low Proliferative Capacity That Produce Transforming Growth Factor β and Interleukin-10," Clinical and Diagnostic Laboratory Immunology, Jul. 2001, pp. 695-701, vol. 8, No. 4, © American Society for Microbiology, 7 pages.
Wallace, T. D. et al., "Interactions of Lactic Acid Bacteria with Human Intestinal Epithelial Cells: Effects on Cytokine Production," Journal of Food Protection, 2003, pp. 466-472, vol. 66, No. 3, © International Association for Food Protection, 8 pages.
Sturm, A. et al., "*Escherichia coli* Nissle 1917 Distinctively Modulates T-Cell Cycling and Expansion via Toll-Like Receptor 2 Signaling," Infection and Immunity, Mar. 2005, pp. 1452-1465, vol. 73, No. 3, © American Society for Microbiology, 14 pages.
Nelson, H. S. et al., "Treatment of Anaphylactic Sensitivity to Peanuts by Immunotherapy with Injections of Aqueous Peanut Extract," The Journal of Allergy and Clinical Immunology, 1997, pp. 714-751, vol. 99, No. 6, Part 1, © Mosby-Year Book, Inc., 8 pages.
Canonica, G. W. and Passalacqua, G. et al., "Noninjection Routes for Immunotherapy," The Journal of Allergy and Clinical Immunology, Mar. 2003, pp. 437-448, vol. 111, No. 3, © Mosby, Inc., 12 pages.
Wahn, U., The Wahn Declaration in European Patent No. 2244734, Apr. 18, 2018, Kleinmachnow Germany, 5 pages.
Belz, G., The Belz Declaration (second) in European Patent No. 2244734, Apr. 16, 2018, Melbourne Australia, 3 pages.
European Patent No. 2244734, "Effects of Probiotics on Plasmacytoid Dendritic Cells (pDC)," Experimental Data in Support of EP 2244734 of Murdoch Childrens Research Institute, accessed Apr. 2018, 4 pages.
European Patent No. 2244734, "Effects of Probiotics on Plasmacytoid Dendritic Cells (pDC)," Experimental Protocol for Clinical Trial Performed in Support of EP 2244734 of Murdoch Childrens Institute, accessed Apr. 2018, 9 pages.
Staden, U. et al., "Specific Oral Tolerance Induction in Food Allergy in Children: Efficacy and Clinical Patterns of Reaction," Allergy, 2007, pp. 1261-1269, vol. 62, © The Authors © Blackwell Munksgaard, 9 pages.
Blumchen, K. et al., "Oral Peanut Immunotherapy in Children with Peanut Anaphylaxis," The Journal of Allergy and Clinical Immunology, Jul. 2010, pp. 83-91.e1, vol. 126, No. 1, © American Academy of Allergy, 10 pages.
Novak, N. et al., "The Immune Privilege of the Oral Mucosa," Trends in Molecular Medicine, Apr. 7, 2008, pp. 191-198, vol. 14, No. 5, © Elsevier Inc., 8 pages.
Tang, M. L., The Tang Declaration in European Patent No. 2244734, May 18, 2018, Melbourne Australia, 7 pages.
Belz, G., The Belz Declaration (third) in European Patent No. 2244734, May 18, 2018, Melbourne Australia, 5 pages.
European Patent No. 2811845, "Maternal Supplement to Enhance Immune System of an Infant," The Opposition Division Decision at the oral proceedings dated Nov. 10, 2017, 26 pages.
De Jonge, J.D. et al., "Lactobacillus casei Shirota Does Not Decrease the Food Allergic Response to Peanut Extract in Brown Norway Rats," Toxicology, 2008, pp. 140-145, No. 249, © Elservier Ireland Ltd., 6 pages.
Garssen, J., The Garrsen Declaration in European Patent No. 2244734, Apr. 19, 2018, 7 pages.
Jahnsen, F. L., "Experimentally Induced Recruitment of Plasmacytoid (CD123$^{high}$) Dendritic Cells in Human Nasal Allergy," The Journal of Immunology, 2000, pp. 4062-4068, vol. 165, © The American Association of Immunologists, 7 pages.
Van Den Heuvel, M. M. et al., "Functional and Phenotypic Differences of Monocyte-Derived Dendritic Cells From Allergic and NonAllergic Patients," The Journal of Allergy and Clinical Immunology, Jan. 1998, pp. 90-95, vol. 101, No. 1, Part 1, © Mosby Inc., 6 pages.
Frischmeyer-Guerrerio, P.A. et al, "Dendritic Cell and T Cell Responses in Children with Food Allergy," Clinical & Experimental Allergy, Jan. 2011, pp. 1-18 (available in final edited form of Journal as pp. 61-71), vol. 41(1), NIH Public Access Author Manuscript PMC 2012, 18 pages.
Latvala, S. et al., "Potentially Probiotic Bacteria Induce Efficient Maturation but Differential Cytokine Production in Human Monocyte-Derived Dendritic Cells," World Journal of Gastroenterology, Sep. 28, 2008, pp. 5570-5583, vol. 14(36), @ The WJG Press, 14 pages.
Christensen, H. R. et al., "Lactobacilli Differentially Modulate Expression of Cytokines and Maturation Surface Markers in Murine Dendritic Cells," The Journal of Immunology, 2002, pp. 171-178, vol. 168, © The American Association of Immunologists, 9 pages.
Gilliet, M. et al., "Plasmacytoid Dendritic Cells: Sensing Nucleic Acids in Viral Infection and Autoimmune Diseases," Nature Reviews: Immunology, Aug. 2008, pp. 594-606, vol. 8, © Macmillan Publishers Limited, 13 pages.
European Patent No. 2244734 B1, "A Method of Inducing Tolerance to an Allergen," Patentee's Submissions, Opposition by Nestec S.A., May 29, 2018, 1 page.
European Patent No. 2244734 B1, "A Method of Inducing Tolerance to an Allergen," Patentee's Submissions, Opposition by Nestec S.A., May 18, 2018, 9 pages.
European Patent No. 2244734 B1, "A Method of Inducing Tolerance to an Allergen," Patentee's Submissions, Opposition by Nestec S.A., Apr. 19, 2018, 17 pages.
European Patent No. 2244734 B1, "A Method of Inducing Tolerance to an Allergen," Patentee's Submissions, Opposition by N.V. Nutricia, Apr. 19, 2018, 5 pages.
European Patent No. 2244734 B1, "A Method of Inducing Tolerance to an Allergen," Response to the Preliminary Opinion of the Opposition Division, Apr. 19, 2018, 67 pages.
European Patent No. 2244734 B1, "A Method of Inducing Tolerance to an Allergen," Notification Concerning the Date of Oral Proceedings, Mar. 8, 2018, 1 page.
European Patent No. 2244734 B1, "A Method of Inducing Tolerance to an Allergen," Opponent's Response to Request for Postponement x2, Mar. 5, 2018, 4 pages.
European Patent No. 2244734 B1, "A Method of Inducing Tolerance to an Allergen," Letter Requesting Postponement of Oral Proceedings, Feb. 27, 2018, 5 pages.
European Patent No. 2244734 B1, "A Method of Inducing Tolerance to an Allergen," Summons to Attend Oral Proceedings, Dec. 13, 2017, 16 pages.
European Patent No. 2244734 B1, "A Method of Inducing Tolerance to an Allergen," Patentee Response to Notices of Opposition, Jul. 25, 2017, 52 pages.
European Patent No. 2244734 B1, "A Method of Inducing Tolerance to an Allergen," Communication of a Notice of Opposition dated Feb. 16, 2017, Notice of Opposition by Nestec S.A. dated Jan. 31, 2017, 20 pages.
European Patent No. 2244734 B1, "A Method of Inducing Tolerance to an Allergen," Communication of a Notice of Opposition dated Dec. 23, 2016, Notice of Opposition by N.V. Nutricia dated Dec. 14, 2016, 17 pages.

* cited by examiner

METHOD OF INDUCING TOLERANCE TO AN ALLERGEN

CROSS-REFERENCES TO RELATED APPLICATIONS

This application is a continuation of U.S. patent application Ser. No. 12/865,499, filed Dec. 20, 2010, which application is a 371 National Stage of International Patent Application No. PCT/AU2009/000104, filed Jan. 30, 2009, which application claims priority benefit under 35 U.S.C. 119(a) to Australian Provisional Patent Application No. 2008900463, filed Feb. 1, 2008, each of which is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention relates generally to the field of allergies. More particularly, the present invention provides a method for treating an allergy in a subject by inducing tolerance to an allergen associated with the allergy. Medicinal kits useful in protocols to induce tolerance or reduce intolerance in a subject also form part of the present invention.

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Rates of allergic disease have risen exponentially since 1980. While the prevalence of asthma, eczema and rhinitis may be stabilizing, food allergy and anaphylaxis continue to rise (Gupta et al, *Thorax* 62(1):91-96, 2007; Robertson et al, *Med J Aust* 180(6):273-276, 2004). In the UK, hospital admissions for food allergy and anaphylaxis have increased 500% and 700% respectively from 1991 to 2005 (Gupta et al, supra 2007). Prevalence of childhood peanut allergy has doubled between 1997 and 2002 (Sicherer et al, *J Allergy Clin Immunol* 112(6):1203-1207, 2003). Data from the Australian Institute of Health and Welfare show similar trends (Mullins, *Med J Aust* 186(12):618-621, 2007). Allergic disorders are now the most common chronic diseases affecting children in Western societies. It is estimated that 5%-8% of children have a food allergy (Bock, *Pediatrics* 79(5):683-688, 1987; Young et al, *Lancet* 343(8906):1127-1130, 1994), and 1.5% of children have peanut allergy (Grundy et al, *J Allergy Clin Immunol* 110(5):784-789, 2002).

Foods are the commonest triggers of severe allergic reactions (anaphylaxis) [Kemp et al, *Arch Intern Med* 155 (16):1749-1754, 1995]. Peanut allergy is of particular concern as reactions to peanuts are usually severe, involving two or more organ systems in 41% of peanut allergic subjects, and involving the respiratory system (anaphylaxis) in 42% of peanut allergic subjects (Sicherer et al, *Pediatrics* 102(1):199-205, 1998). Reactions to peanuts caused 27% (Pumphrey, *Curr Opin Allergy Cin Immunol* 4(4):285-290, 2004) to 30% (Bock et al, *J Allergy Clin Immunol* 107(1): 191-193, 2001) of deaths from food induced anaphylaxis. The threshold dose for reaction to peanut is often low—subjective and objective symptoms may be induced by as little as 100 μg (<1/1000th of a peanut) and 2 mg of peanut protein (<1/100th of a peanut), respectively (Hourihane et al, *J Allergy Clin Immunol* 100(5):596-600, 1997). In double blind placebo controlled peanut challenges, 50% of peanut allergic subjects reacted to 3 mg of peanut protein (1/100th of a peanut) [Wensing et al, *J Allergy Clin Immunol* 110(6): 915-920, 2002]. Furthermore, subjects with severe reactions to peanut tend to react to lower doses of peanut than those with mild symptoms (Wensing et al, supra 2002). Therefore, most allergic reactions to peanut are severe, reactions may occur to low doses of allergen, and peanut induced reactions account for a large proportion of deaths from food allergy.

Most cases of peanut allergy first present in early childhood between the ages of 14 and 24 months (Sicherer et al, supra 1998). Unlike allergy to milk and egg which generally resolve by late childhood, peanut allergy usually persists. Only 18% (Hourihane et al, *Bmj* 316(7140):1271-1275, 1998) to 21% (Skolnick et al, *J Allergy Clin Immunol* 107(2):367-374, 2001) of children outgrow their peanut allergy (spontaneous development of tolerance), and there are no reliable predictors for resolution (Skolnick et al, supra 2001; Hourihane et al, supra 1998). Accidental ingestions of peanut in children with peanut allergy are common—50% within 1 year and 75% within 5 years (Bock and Atkins, *J Allergy Clin Immunol* 83(5):900-904, 1989). Most reactions from accidental ingestion are life threatening (Vander Leek et al, *J Pediatr* 137(6):749-755, 2000). Only 25% of peanut allergic patients were able to achieve complete avoidance without reaction in a five year period (Bock and Atkins, supra 1989). Therefore, patients with peanut allergy remain at significant ongoing risk of severe reactions.

There has been no effective long term treatment for food allergy. Management involves avoidance of the food concerned, early recognition of symptoms of an allergic reaction and initiation of appropriate emergency treatment of allergic reactions, particularly anaphylaxis. Adrenaline is the first line therapy for anaphylaxis and is available as a self injectable device, the EpiPen (Registered)/EpiPen Jr (Registered) in Australia (and other devices in USA). The EpiPen (Registered) or EpiPen Jr (Registered) must be replaced regularly (12-18 months) and requires specific training in its use (Mehr et al, *Paediatr Allergy Immunol* 18(5):448-452, 2006). As the majority of reactions to peanut are severe, most children with peanut allergy are prescribed an EpiPen (Registered) which must be carried with them at all times. The EpiPen (Registered) should be administered if accidental exposure results in a severe reaction involving the respiratory or cardiovascular systems (anaphylaxis). However, most patients who have been prescribed an EpiPen (Registered) fail to use it at the time of a severe allergic reaction. Only 71% of patients prescribed an EpiPen had their EpiPen with them, 10% of these had expired, and only 32% were able to demonstrate its correct use (Sicherer et al, *Pediatrics* 105(2):359-362, 2000). The burden of living with peanut allergy and its management is significant—children with peanut allergy are reported by their parents to have a poorer quality of life than children with rheumatological conditions (Primeau et al, *Clin Exp Allergy* 30(8):1135-1143, 2000). Therefore, for peanut allergy, the high risk of repeated severe life-threatening reactions and the limited reliability of EpiPen (Registered) being used for the treatment of acute reactions in the community highlight the need for long term treatment options that can achieve immune modulation and tolerance.

The mechanisms leading to the development of food allergy remain poorly understood. It is considered that food allergy is caused by a failure of oral tolerance. Oral tolerance can be induced by either a single high dose exposure to antigen or by repeated low dose exposures to antigen. High dose tolerance involves Fas-mediated apoptosis or anergy, while low dose tolerance is mediated by regulatory T cells (Treg). Recent studies suggest that anergy and induction of Treg may not be distinct mechanisms for tolerance, and most studies now focus on the role of Treg (reviewed in [Strobel and Mowat, Curr Opin Allergy Clin Immunol 6(3):207-213, 2006]). Several Treg subsets have been identified including Th3 cells, Tr1 cells, and CD4+CD25+ Treg. Th3 cells produce TGFβ and variable amounts of IL-4 and IL-10 (Chen et al, Science 265(5176):1237-1240, 1994). Tr1 cells secrete IL-10 (Groux et al, Nature 389(6652):737-742, 1997). CD4+CD25+ Treg express the transcription factor forkhead box P3 (FOXP3) and mediate their suppressive effects in part by cell surface bound TGFβ and to a lesser extent IL-10 (Chung et al, J Leukoc Biol 77(6):906-913, 2005). CD4+CD25+ Treg arise predominantly in the thymus, but may also develop in mesenteric lymph nodes, Peyer's patches and peripheral lymph nodes where they play a role in mucosal tolerance (Chung et al, supra 2005). Treg and the regulatory cytokines TGFβ and IL-10 have been shown to play important roles in oral tolerance induction and in food allergy. In a mouse model of food allergy, mice tolerized to β-lactoglobulin had higher numbers of antigen specific IgA secreting cells in Peyer's patches and higher levels of fecal IgA, as well as increased TGFβ and IL-10 production by Peyer's patch T cells as compared to sensitized mice (Frossard et al, J Allergy Clin Immunol 114(2): 377-382, 2004).

Evidence of a role for Treg in tolerance induction and food allergy is also observed in human studies. Children with food allergy have fewer TGFβ+ lymphocytes in the duodenal epithelium and lamina propria (Perez-Machado et al, Eur J Immunol 33(8):2307-2315, 2003), and show reduced TGFβ expression by milk specific duodenal lymphocytes (Beyer et al, J Allergy Clin Immunol 109(4):7070-713, 2002). Similar findings have been reported for patients with non-IgE mediated food allergies (food protein induced enterocolitis) [Chung et al, J Allergy Clin Immunol 109(1): 150-154, 2002]. In subjects with cow's milk allergy, resolution of allergy was associated with increased numbers of CD4+CD25+ T cells and reduced β-lactoglobulin induced proliferation compared to those with ongoing allergy (Karlsson et al, J Exp Med 199(12):1679-1688, 2004). In vitro depletion of these CD4+CD25+ cells led to increased β-lactoglobulin induced proliferation suggesting that induction of oral tolerance was related to increased CD4+CD25+ cells Treg (Karlsson et al, supra 2004). Oral tolerance is also associated with increased IFNγ (Tureanu et al, J Clin Invest 111(7):1065-1072, 2003). Comparison of peanut specific immune responses in normal children, children with peanut allergy, and peanut allergic children who had outgrown their allergy showed Th2 skewed responses in peanut allergy and Th1 skewed responses in oral tolerance (normal children and children who outgrew their peanut allergy) [Tureanu et al, supra 2003). These findings suggest that food allergy is associated with loss of tolerance, reduced Treg and TGFβ, as well as reduced Th1 and increased Th2 responses.

Immunotherapy is used for the long term treatment of asthma, allergic rhinitis and insect venom anaphylaxis. Subcutaneous immunotherapy (SCIT) has been shown to reduce clinical symptoms and induce prolonged tolerance to allergens by modulation of immune responses (Norman, J Allergy Clin Immunol 113(6):1013-1023, 2004; Schmidt-Weber and Blaser, Springer Semin Immunopathol 25(3-4): 377-390, 2004). Mechanistic studies have shown that SCIT induces Treg and restores the disturbed balance of Th1/Th2 effector cells in allergic patients. SCIT leads to reduced allergen specific IgE, elevated allergen specific IgG4, reduced Th2 cytokine expression (IL-4, IL-5), and in most studies increased Th1 cytokine expression (IFNγ) [Norman, supra 2004; Schmidt-Weber and Blaser, supra 2004]. These effects have been shown to be mediated by increased numbers of CD4+CD25+ Treg, and induction of antigen specific CD4+CD25+ Treg with suppressive activity that is mediated by production of IL-10 and/or TGFβ (Norman, supra 2004; Schmidt-Weber and Blaser, supra 2004). Other immunological effects of SCIT include increased apoptosis of allergen specific Th2 cells, reduced tissue mast cell numbers and reduced serum levels of TNFα and IL-1β (Norman, supra 2004). Sublingual immunotherapy (SLIT) has also been shown to be effective in reducing clinical symptoms in respiratory allergy (asthma, rhinitis), however, immunological effects are less well characterized. Increased specific IgG4 and reduced specific IgE have been reported in some but not all studies (Norman, supra 2004). Oral immunotherapy (OIT) has not been consistently effective when used for the treatment of respiratory allergy and was largely abandoned for treatment of these conditions.

Various immunotherapy approaches have been attempted for the treatment of food allergy. Treatment with a humanized anti-IgE antibody was shown to increase the threshold dose required to induce a reaction, however, this approach is expensive and only provides a short term benefit without modifying the natural history of disease (Leung et al, N Engl J Med 348(11):986-993, 2003). SCIT for peanut anaphylaxis was effective in inducing desensitization and increasing the threshold dose required to induce a reaction (from 178 mg to 2805 mg, or from half a peanut to nine peanuts) in subjects who were able to continue on maintenance therapy (Nelson et al, J Allergy Clin Immunol 99(6 Pt1):744-751, 1997). However, serious systemic reactions were frequent (39% during maintenance) and this approach has been abandoned. Peptide and mutated protein SCIT are being investigated to avoid systemic reactions, however, translation to the clinic setting has been slow. SLIT has been used for the treatment of food allergy. A double blind placebo controlled study of SLIT with hazelnut extract for four months in 41 adults with hazelnut allergy resulted in an increased threshold for reaction in the active treatment group (from 2.29 g to 11.56 g) but not the placebo group (3.49 g to 4.14 g). 50% of the treatment group as compared to 9% of the placebo group were able to tolerate 20 g of hazelnut during oral challenge performed 8-12 weeks after immunotherapy had been discontinued, indicating long-lasting tolerance. As further evidence of immune tolerance, the active treatment group demonstrated increased serum levels of IL-10 and hazelnut specific IgG. SLIT with fresh kiwi pulp also resulted in prolonged clinical tolerance to kiwi in a 29 year old female who demonstrated protective effects from SLIT even after it had been discontinued for a period of four months (Kerzl et al, J Allergy Clin Immunol 119(2):507-508, 2007). These findings confirm the potential for SLIT as a treatment for food allergy in adults with evidence of immunomodulatory effects and prolonged clinical protection.

However, a major disadvantage of SLIT limiting its applicability in children is the need to hold the extract under the tongue for a period of time (1-3 minutes) before swallowing or discharging (Enrique et al, *J Allergy Clin Immunol* 116(5):1073-1079, 2005; Kerzl et al, supra 2007). OIT offers the advantage of improved acceptability and compliance in children (Buchanan et al, *J Allergy Clin Immunol* 119(1): 199-205, 2007).

OIT has been used successfully for the treatment of food allergy. Case reports describe desensitization with OIT in milk allergy (Nucera et al, *Dig Dis Sci* 45(3):637-641, 2000; Bauer et al, *Allergy* 54(8):894-895, 1999). A 12 year old girl was desensitized to cow's milk and remained on OIT indefinitely (Bauer et al, supra 1999). A six year old girl with cow's milk allergy was desensitized to milk following four months of milk OIT, and experienced dramatic immunological changes including complete loss of SPT reaction to cow's milk, reduced serum levels of milk specific IgE, increased serum levels of milk specific IgG4 and IgA, as well as increased IFNγ and decreased IL-4 production in β-lactoglobulin stimulated PBMC cultures (Nucera et al, supra 2000). This suggests that OIT may induce tolerance in some circumstances. A large case control study of OIT in 51 patients aged 3-55 years with various food allergies showed successful desensitization in 83% (45/54) of subjects who remained on daily OIT (Patriarca et al, *Aliment Pharmacol Ther* 17(3):459-465, 2003). A reduction in peanut specific IgE and increase in peanut specific IgG4 was demonstrated suggesting the possibility of tolerance induction but this was not examined specifically (Patriarca et al, supra 2003). A double blind RCT of milk OIT (200 ml maintenance dose) for six months in 21 children with milk allergy reported successful desensitization to milk in 71% (15/21) [tolerated 200 ml of milk on a daily basis], and partial desensitization in 3/21 (14%) [tolerated 40-80 ml of milk] (Meglio et al, *Allergy* 59(9):980-987, 2004). None of the children demonstrated a reduction in milk specific IgE suggesting that tolerance was not achieved. In all of these previous studies, it is not certain whether OIT was effective in inducing tolerance since DBPC food challenges were not performed after immunotherapy was discontinued. Rolinck-Werninghaus reported two patients in whom discontinuation of milk or egg OIT following 37 wk and 41 wk of OIT respectively resulted in loss of desensitization, indicating that tolerance had not been achieved (Rolinck-Werninghaus et al, *Allergy* 60(10):1320-1322, 2005).

Studies and investigations aimed at developing protocols to manage allergic disorders have been focused on prevention rather than treatment and have been based on animal models which poorly replicate the human allergic disease condition (e.g.: Schabussora and Widermann, *Curr Opin Allergy Clin Immunol* 8(6):557-564, 2008; Daniel et al, *Allergy* 52(11):1237-1242, 2007; and Shida et al, *Clin Exp Allergy* 32:563-570, 2002). Neither a prevention nor treatment protocol based on probiotics or prebiotics alone has achieved large scale success. Initial studies of probiotics or prebiotics for the prevention of eczema had provided promising results (Osborne and Sinn, *Probiotics in infants for prevention of allergic disease and food hypersensitivity* (Review), Cochrane Database *Syst Rev* Art No. CD006475, 2007; Osborne and Sinn, *Probiotics in infants for prevention of allergic disease and food hypersensitivity* (Review), Cochrane Database *Syst Rev* Art No. CD006474, 2007). However, probiotics for the treatment of eczema has not proven successful as have the use of probiotics or prebiotics alone for the prevention or treatment of food allergy (Boyle et al, *Syst Rev*, Oct. 8, 2008 Issue 4, CD006135).

New strategies to treat allergies which enhance tolerance induction are required.

BRIEF SUMMARY OF THE INVENTION

The present invention contemplates the use of allergen immunotherapy and biotic agents to induce tolerance in subjects, such as humans and non-human animals, to the allergen. "Allergen immunotherapy" includes the administration of the allergen or an antigen component or modified form thereof by any means such as by oral, subcutaneous, sublingual, inhalation, intravenous, rectal or intraperitoneal means.

The biotic agent is generally a probiotic agent comprising a eukaryotic or prokaryotic organism such as a species of *Lactobacillus, Bifidobacterium, Escherichia, Bacillus, Saccharomyces* and/or *Streptococcus* or a prebiotic agent which facilitates growth and maintenance of microflora in a subject being treated. In one embodiment, the probiotic agent is *Lactobacillus rhamnosus*. In another embodiment, the prebiotic agent is an oligosaccharide or soluble or insoluble fibre.

The allergen immunotherapy and biotic agent(s) may be sequentially administered or given simultaneously. Reference to "administration" includes sequential or simultaneous administration of the allergen and probiotic and/or prebiotic.

The allergen includes inter alia any food, drug, environmental, biological and chemical allergens. Food allergies such as to milk, eggs, legumes (e.g. peanuts), tree nuts, fish, shellfish, soy and wheat and bread are particularly contemplated herein.

Hence, treatment protocols to induce allergen tolerance or reduce intolerance in a subject in need thereof forms part of the present invention. The term "induce tolerance" includes reducing sensitivity to an allergen and reducing sensitivity to an allergy. In particular, the present invention is directed to reducing intolerance to an allergen by the sequential or simultaneously administration of an allergen and a biotic to a subject in need of treatment. The "biotic" may be a probiotic or a prebiotic or both.

Accordingly, one aspect of the present invention contemplates a method for inducing tolerance in a subject to an allergen, the method comprising administering to the subject an amount of allergen or antigenic fragment or component or analog of the allergen and a biotic agent effective to induce tolerance in the subject to the allergen.

The present invention further provides a method for reducing a subject's sensitivity to an allergy, the method comprising administering to the subject a biotic agent in conjunction with an allergen associated with the allergy or an antigenic fragment or component or analog of the allergen for a time and under conditions sufficient for a level of tolerance to be induced in the subject.

The present invention is particularly directed to a method for treating allergen intolerance in a subject, the method comprising administering sequentially or simultaneously to the subject, a biotic and the allergen or an antigenic component or fragment or analog thereof in an amount effective to induce tolerance to the allergen.

The present invention further directed to a method for inducing tolerance to an allergy in a subject in need thereof, the method comprising administering sequentially or simultaneously to the subject, a biotic and an allergen associated with the allergy or an antigenic component or fragment or analog thereof in an amount effective to induce tolerance to the allergy.

Whilst not intending to limit the present invention to any one theory or mode of action, the combined effect of the biotic agent with allergen immunotherapy is proposed to increase Th1 responses compared to Th2 responses.

By 'subject" is meant a human or non-human animal such as a companion animal, livestock animal or captured wild animal. The subject is generally in need of treatment.

Formulations comprising a biotic agent as well an allergen or an antigenic fragment or component or analog thereof and one or more pharmaceutically acceptable excipients, carriers and/or diluents are also provided.

The present invention also provides a medicinal kit comprising in compartmental form a first compartment or series of compartments comprising biotic agents and a second compartment or series of compartments comprising an allergen or source of allergen or antigenic fragments, components or analogs thereof with instructions for use.

The instructions for use include a medicinal protocol to use the biotic agents in conjunction with an allergen or source of allergen to induce tolerance or reduced sensitivity to an allergen.

As indicated above, the term "biotic" is used to encompass a probiotic and a prebiotic. Both a probiotic and a prebiotic may also be administered in a sequential or simultaneous manner.

BRIEF DESCRIPTION OF THE DRAWINGS

NOT APPLICABLE

DETAILED DESCRIPTION OF THE INVENTION

Throughout this specification, unless the context requires otherwise, the word "comprise", or variations such as "comprises" or "comprising", is understood to imply the inclusion of a stated element or integer or group of elements or integers but not the exclusion of any other element or integer or group of elements or integers.

As used in the subject specification, the singular forms "a", "an" and "the" include plural aspects unless the context clearly dictates otherwise. Thus, for example, reference to "a biotic agent" includes a single biotic agent, as well as two or more biotic agents (which includes two or more probiotics or prebiotics or a probiotic and a prebiotic); reference to "an allergen" includes a single allergen, as well as two or more allergens; reference to "the invention" includes single and multiple aspects of an invention; and so forth.

The present invention provides a medicinal protocol for treating a subject with an allergy by generating tolerance in the subject to an allergen. The protocol comprises providing the subject with a biotic agent and the allergen or a modified form thereof to which tolerance is desired.

"Inducing tolerance" includes reducing sensitivity to an allergen or an allergen associated with an allergy. Hence, it encompasses reducing sensitivity to an allergy as well as reducing intolerance to an allergen—induced allergy.

Hence, the present invention provides a method for treating allergen intolerance in a subject, the method comprising administering sequentially or simultaneously to the subject, a biotic and the allergen or an antigenic component or fragment or analog thereof in an amount effective to induce tolerance to the allergen.

The allergen is provided to initiate and/or boost and/or maintain an immune response. Reference to an "allergen" includes any substance which is capable of stimulating a typical hypersensitivity reaction in atopic subjects. Allergens contemplated herein include any substance in food, drugs, perfume, plants, the environment or biological systems (e.g. prokaryotic or eukaryotic cells or viruses), as well as chemical allergens. Types of allergens include animal products (e.g. cats, fur and dander, cockroach calyx, dust mite excretion); drugs (e.g. penicillin, sulfonamides, salicylates (also found naturally in numerous fruits), local anaesthetics); foods (e.g. celery, celeriac, corn or maize, eggs (typically albumen, the white), fruit, pumpkin, legumes (e.g. beans, peas, peanuts, soybeans), milk, seafood, sesame, soy, tree nuts (e.g. pecans almonds), wheat, insect stings (e.g. bee sting venom, wasp sting venom, mosquito stings); mold spores, latex, metal; and plant pollens (e.g. grass—ryegrass, timothy-grass, weeds—ragweed, plantago, nettle, *Artemisia, vulgaris, chenopodium album*, sorrel, trees—birch alder, hazel, hornbeam, aesculus, willow, poplar, platanus, tilia, olea).

The present invention is particularly directed to food allergens such as found in milk, eggs, peanuts, tree nuts, fish, shellfish, soy and wheat.

In one embodiment, the present invention is directed to inducing tolerance to legume allergens and in particular peanut allergens.

Reference to the "allergen" includes the allergen in a purified or substantially purified or isolated form or when incorporated as part of a substance such as food, a biological system, or chemical composition. Furthermore, the allergen to be administered may also be a modified form including an antigenic derivative or component or homologue or chemical analog. An "allergen" encompasses a mixture of allergens as well as genetically modified or chemically modified allergens.

The present invention is directed to inducing tolerance or reducing sensitivity to an allergen or an allergy associated with the allergen as well as reducing intolerance to an allergen-induced allergy.

The term "biotic" encompasses both a probiotic and a prebiotic. A probiotic is generally a live eukaryotic or a prokaryotic organism which has a beneficial property when given to a subject. In one aspect, the probiotic complements the existing microflora in the subject. Hence, the probiotic agent is a live microorganism which can confer a health benefit to a host subject. The probiotic agent may be a culture of microorganisms or provided in a dietary supplement or may be freeze dried and reconstituted prior to use. A prebiotic is an agent which facilitates or confers growth, maintenance and/or beneficial properties of or on the subject's microflora. A prebiotic includes an oligosaccharide and soluble or insoluble fibre material. A probiotic and a prebiotic may also be sequentially or simultaneously administered.

Examples of probiotic agents include species of *Lactobacillus, Escherichia, Bacillus, Bifidobacterium, Saccharomyces* and *Streptococcus*.

Particularly useful probiotic agents are from the genus *Lactobacillus* such as *Lactobacillus acidophilus* NCFM, *Lactobacillus casei, Lactobacillus casei* Shirota, *Lactobacillus casei* immunitass, *Lactobacillus johnsonii, Lactococcus lactis, Lactobacillus plantarum, Lactobacillus reuteri, Lactobacillus rhamnosus, Lactobacillus salivarius* and *Lactobacillus helvetirus*.

*Lactobacillus rhamnosus* GG (LGG) is considered herein to be a particularly useful probiotic agent.

The microorganisms may be naturally occurring, attenuated or genetically modified to introduce new or to alter existing traits. In one embodiment, the probiotic has been genetically modified to introduce an allergen gene or part or fragment or portion thereof which is expressed to produce recombinant microorganisms which release or expose the subject's immune system to the allergen or an antigenic fragment thereof. Hence, the probiotic and allergen may be given to the subject as a single entity. As indicated above, a probiotic and a prebiotic may also be administered, together with the allergen or the allergen may be produced by the probiotic.

Hence, the present invention provides a method for inducing tolerance in a subject to an allergen, the method comprising administering to the subject an amount of allergen or antigenic fragment, compound or analog thereof and a biotic agent effective to induce tolerance in the subject to the allergen.

In another embodiment, the present invention contemplates a method for inducing tolerance in a subject to an allergen, the method comprising administering to the subject an amount of probiotic modified to produce an allergen or fragment or homolog thereof in an amount effective to induce tolerance in the subject to the allergen.

In one particular embodiment, the allergen is a legume such as a peanut.

Hence, another aspect of the present invention contemplates a method for inducing tolerance in a subject to a legume allergen, the method comprising administering to the subject an amount of the legume allergen or an antigenic fragment, component or analog thereof and a biotic agent effective to induce tolerance in the subject to the legume allergen.

One or more allergens may be administered generally at an amount which does not cause distress to the subject such as in the form of anaphylaxis. As indicated above, the legume allergen may also be produced by a probiotic form of the biotic.

In a particular embodiment, probiotic is a species of *Lactobacillus*.

Another aspect of the present invention contemplates, therefore, a method for inducing tolerance in a subject to a legume allergen, the method comprising administering to the subject an amount of the legume allergen or an antigenic fragment, component or analog thereof and a biotic agent is a probiotic agent selected from the list consisting of *L. acidophilus* NCFM, *L. casei*, *L. casei* Shirota, *L. casei* immunitass, *L. johnsonii*, *L. lactis*, *L. plantarum*, *L. reuteri*, *L. rhamnosus*, *L. salivarius* and *L. helvetirus* effective to induce tolerance in the subject to the allergen.

Yet another aspect of the present invention contemplates, therefore, a method for inducing tolerance in a subject to a legume allergen, the method comprising administering to the subject an amount of the legume allergen or an antigenic fragment, component or analog thereof and a biotic agent is a prebiotic agent selected from the list consisting of an oligosaccharide and a fibre effective to induce tolerance in the subject to the allergen.

In a particular embodiment, the probiotic is *L. rhamnosus* or a modified form thereof. In another particular embodiment, the prebiotic is an oligosaccharide or a soluble or insoluble fibre.

Another aspect of the present invention contemplates a method for inducing tolerance in a subject to a peanut allergen, the method comprising administering to the subject an amount of the peanut allergen or an antigenic fragment, component or analog thereof and a biotic agent effective to induce tolerance in the subject to the peanut allergen.

The present invention further contemplates, a method for inducing tolerance in a subject to a peanut allergen, the method comprising administering to the subject an amount of the peanut allergen or an antigenic fragment, component or analog thereof and a biotic agent selected from the list consisting of *L. acidophilus* NCFM, *L. casei*, *L. casei* Shirota, *L. casei* immunitass, *L. johnsonii*, *L. lactis*, *L. plantarum*, *L. reuteri*, *L. rhamnosus*, *L. salivarius* and *L. helvetirus* effective to induce tolerance in the subject to the allergen.

Yet another aspect of the present invention provides a method for inducing tolerance in a subject to a peanut allergen, the method comprising administering to the subject an amount of the peanut allergen or an antigenic fragment, component or analog thereof and a prebiotic agent selected from the list consisting of an oligosaccharide and a fibre effective to induce tolerance in the subject to the allergen.

As indicated above, the fibre may be soluble or insoluble.

A method is also provided for reducing a subject's sensitivity to an allergy, the method comprising administering to the subject a biotic agent in conjunction with an allergen associated with the allergy or an antigenic fragment or component or analog of the allergen for a time and under conditions sufficient for a level of tolerance to be induced in the subject.

The "administering" includes sequential and simultaneous administration of a probiotic and/'or prebiotic and allergen.

Whilst not intending to limit the present invention to any one theory or mode of action, the combined effect of the biotic agent with allergen immunotherapy is proposed to increase Th1 responses compared to Th2 responses.

The present invention also provides a medicinal kit comprising in compartmental form a first compartment or series of compartments comprising biotic agents and a second compartment or series of compartments comprising an allergen or source of allergens or antigenic fragments, components or analogs thereof with instructions for use.

The instructions for use include a medicinal protocol to use the biotic agents in conjunction with an allergen or source of allergen to induce tolerance or reduced sensitivity to an allergen.

An "effective amount" or "therapeutically effective amount" means an amount necessary at least partially attain the desired immunological effect of tolerance or to delay the onset or inhibit progression or halt altogether, the onset of progression of an allergic response to an allergen in the subject in need of treatment. It is expected that the amount will fall in a relatively broad range that can be determined through routine trials. The "effective amount" relates to the allergen and biotic, individually or combined. Conveniently, administration of at least the allergen includes a "rush" amount followed by a "maintenance" amount. Examples of effective amounts range from 0.05 mg to 2000 mg per day, week or month. For peanut allergens, 0.1 mg to 300 mg per day is effective.

The present invention in a particular aspect is directed to treatment of a subject in need thereof rather than prophylaxis. That said, in another aspect, a prophylactic component is contemplated.

As used herein, the terms "treating" or "treatment" encompass the administration of an agent which induces tolerance to an allergen.

The present invention is further directed to a method for inducing a level of tolerance to an allergy in a subject, the method comprising providing to the subject effective amounts of a biotic and an allergen associated with the allergy.

As indicated above, a single allergen may be provided or multiple allergens are provided.

The "level" of tolerance includes complete tolerance or an increased threshold in the amount of allergen to which a subject may be exposed prior to inducing an adverse allergic reaction.

The term "subject" as used herein refers to an animal, particularly a mammal and more particularly a primate including a lower primate and even more particularly, a human who can benefit from the methods of the present invention. Generally, the subject is in need of treatment as the present invention is particularly directed to treatment of an allergen-induced allergy. Genetic testing of subjects or embryos in utero may also identify subjects at risk of developing an allergy. A subject regardless of whether a human or non-human animal or embryo, may be referred to as an individual, subject, animal, patient, host or recipient. The present invention, therefore, has both human and veterinary applications. For convenience, an "animal" specifically includes livestock animals such as cattle, horses, sheep, pigs, camelids, goats and donkeys. With respect to horses, these include horses used in the racing industry as well as those used recreationally or in the livestock industry. The non-human animal may also include a companion animal such as a dog or cat or captured wild animal.

The present invention extends to any subject having an allergy or predisposed to an allergic reaction. Hence, the subject may have a family history, genetic trait or predisposition to the development of an allergy and accordingly may be administered doses of the probiotic and allergen to induce some level of tolerance to the allergen.

The biotic and allergen are given in conjunction with each other. Insofar as the biotic is a probiotic, the allergen or a genetically modified form or fragment thereof, may be produced by the microorganism.

By "in conjunction" is meant simultaneous administration in the same formulation or in two different formulations via the same or different routes or sequential administration by the same or different routes. The term "in conjunction" also includes the use of two or more allergens in the same therapeutic protocol. By "sequential" administration is meant a time difference of from seconds, minutes, hours or days between the administration of the two types of molecules. The biotic and allergen may be administered in any order. The probiotic form of the biotic may also produce the allergen. The biotic (i.e. probiotic and/or prebiotic) may be sequentially or simultaneously administered with the allergen.

As used herein "administering" or "administration" or "providing" an agent to a subject includes delivery via any route such as oral, subcutaneous, sub lingual, nasal, intravenous, anal or intra-peritoneal routes. The biotic may be given over a period of time prior to the allergen vice versa. Alternatively, both agents may be given at approximately the same time.

Standard formulations may be employed for each or either of the biotic and allergen. As indicated above, the biotic may be in freeze dried form which is then reconstituted prior to use or the biotic may be given as a dietary supplement. The freeze dried formulation may also comprise the allergen in a similar form. The biotic may also be given with a source of allergen such as milk, eggs, bread, soy and the like.

The present invention further provides diagnostic assays to monitor immune mechanisms underlying tolerance. Examples of immune mechanisms include monitoring IgE, IgG4 and IgA levels as well as regulatory T-cell levels (Tregs).

The present invention is further described by the following non-limiting Examples.

Example 1

Effects of Probiotic and Allergen
Subject Recruitment, Treatment and Sample Collection Eleven healthy non-atopic adults were treated with $1.8 \times 10^{10}$ CFU LGG (Dicoflor, Dicofarm SpA, Rome) daily for 7 days. ten ml venous blood was harvested prior to treatment and at day 7. Blood samples were collected in polypropylene tubes containing heparinized RPMI tissue-culture medium (Invitrogen, Carlsbad, Calif.).

Preparation of Blood Samples and Cell Culture

Mononuclear cells were separated by density centrifugation and cryopreserved for future batched analyses (Dunstan et al, *J Allergy Clin Immunol* 112:1178-1184, 2003). Two million cells/ml were incubated with or without antigen in AIM-V serum free medium (Invitrogen) for 48 h, or in RPMI with 10% v/v autologous plasma for 6 days in proliferation assays. Heat killed LGG (HKL) was prepared by incubating LGG at 75° C. for 45 minutes and was used at 5:1 HKL to mononuclear cell ratio. OVA (Sigma, St Louis, Mo.) was used at 100 μg/ml. IFNγ-1b (Boehringer Ingelheim, Germany) and LPS (Sigma) were both used at 10 ng/ml. All cell culture reagents were tested for endotoxin contamination (Cape Cod Associates, E. Falmouth, Mass.). OVA required endotoxin removal over polymyxin B columns prior to use (Pierce, Rockford, Ill.).

Flow Cytometry

Cell pellets were stained with fluorochrome-conjugated monoclonal antibodies in 50 μl staining volumes. Lineage cocktail-FITC (anti-CD3, 14, 16, 19, 20, 56), HLA-DR-Peridinin chlorogphyll protein (PerCP), CD123-PE and CD11c– Allophycocyanin (APC) were used to identify DC phenotypes as $CD11c^{hi}CD123w^{lo}$ myeloid DC (mDC), $CD123^{hi}CD11c^{lo}$ plasmacytoid DC (pDC) and $CD11c^{lo}CD123w^{lo}$ immature DC (iDC), CD3-APC, CD4-PerCP, CD25-PE-Cy7 (BD Bioscience, San Jose, Calif.), CD25-FITC and FoxP3-PE (E-Bioscience, San Diego, Calif.) were used to identify $CD25^{hi}FoxP3^{hi}$ T-cell populations. CFSE was used as a cell tracking dye, and aminostiblbamidine methanesulfonate as a viability dye (Molecular Probes, Eugene, Oreg.). CBMC or PBMC were incubated with fluorochrome-labeled antibodies or isotype controls for 30 minutes, and for intracellular staining cells were subsequently permeabilized, fixed and stained with FoxP3-PE antibody or isotype control (E-Bioscience). Data were acquired on a 4-color LSR 1II (BD Bioscience) and analyzed with FACSDiva v4.1 software using well defined gating strategies.

ELISA

Concentrations of IL-10, IFN-γ, IL-13, IL-12p40 and TNF-α were determined n CBMC culture supernatants harvested at 48 h by multiplex cytokine bead assay using a Luminex 100 analyzer (Luminex Corporation, Austin, Tex.). Anti-cytokine beads and matched anti-cytokine biotinylated reporters were used according to the manufacturer's instructions (Millipore, Billerica, Mass.). Data were analyzed with Luminex IS 2.3 Software using a five-parameter regression formula to calculate sample concentrations from standard curves. concentrations of TGF-β1 were evaluated using a commercial human TGF-β1 ELISA kit according to the manufacturer's protocol (BD Biosciences). Supernatants were analyzed undiluted in duplicate with recombinant cytokine as a positive and culture medium as a negative control. TGF-β1 concentrations were determined based on a standard curve generated using the KCjunior v1.40.3 program (Bio-Tek Instruments, Winooski, Vt.) with a four-parameter equation. ELISA data were analyzed both as dichotomous data-detected versus not detected; and as continuous data-mean level in each group.

Real Time PCR

RNA was extracted using the RNAeasy Mini Kit (Qiagen, Hilden, Germany) and reverse transcribed to cDNA using the Superscript First Strand Synthesis System and oligo(dT) primers (Invitrogen). All reactions included a 'RT minus' control with no reverse transcriptase to control for the possibility of contaminating DNA. FoxP3 and IL-4 mRNA were quantified by real time PCR using FAM-labeled Taqman Gene Expression Assays on an ABI Prism 7300HT system (Applied Biosystems, Foster City, Calif.). Eukaryotic translation elongation factor 1 alpha (EEF1A1) which is stably expressed in human mononuclear cell cultures was used as a reference gene (Hamalaninen et al, *Anal Biochem* 299:63-70, 2001). The mean level of gene expression in cDNA samples was expressed as a ratio to mean EEF1A1 expression.

Statistics

The clinical trial was designed with a sample size of 250 in order to have 90% power to detect a 40% difference in eczema risk between probiotic and placebo groups. Secondary outcomes included immune outcomes reported herein. All available CBMC samples were evaluated and primary analyses were by intention to treat. Data were assessed using histograms and skewed data were $\log_0$ transformed. Parametric paired data were analyzed using the paired t-test, and non-parametric paired data using Wilcoxon signed rank test and Sign test. Parametric unpaired data were analyzed using the independent t-test, and non-parametric unpaired data using Mann Whitney U test. Continuous data are presented as arithmetic means±1 SEM, or medians with inter-quartile ranges. Categorical data were analyzed using $X^2$ test or Fisher's exact test. P value <0.05 was considered statistically significant, with due caution in interpreting the results of multiple comparisons. Where the significance of findings was unclear a sensitivity analysis was undertaken by excluding participants in whom: (1) treatment compliance data (returned capsule counts) were not available (n=9); (ii) capsule counts suggested compliance levels <50% (n=2); or (iii) no treatment capsules were taken due to premature delivery between randomization and 36 weeks gestation (n=1). analyses were performed using SPSS v 16.0 for Windows (SPSS Inc., Chicago, Ill.).

Effects of LGG Treatment on BPMC Proliferation

The effects of orally administered LGG were evaluated in healthy adults. PBMC were harvested from 11 adults prior to and upon completion of 7 days LGG treatment. Treatment was associated with a 30% reduction (95% CI 11 to 50%; P=0.03) in mean CD4$^+$ T-cell proliferative response to heat killed LGG (HKL) compared with proliferative responses from the same subjects before LGG treatment. In contrast, there was no changed in CD4$^+$ T-cell proliferation to OVA (P=0.2) or medium alone (P=0.06) after LGG treatment.

Effects of LGG Treatment on DC Phenotype

DC phenotype was investigated in cultured PBMC harvested from adults before and after LGG treatment. Plasmacytoid DC (pDC) increased from 3.20% to 5.29% of total DDC (P=0.02) after LGG treatment, in PBMC cultured for 48 h with HKL. A trend towards increased ratio of pDC to myeloid (mDC) was also seen after LGG treatment in PBMC cultured with HKL (mean ratio 0.36 pre-treatment, 0.58 post-treatment; P=0.07). LGG treatment was not associated with any significant change in DC phenotype in PBMC cultured with OVA or medium alone.

The data show that oral administration of LGG to healthy adults leads to systemically detectable changes in T-cell proliferative responses and DC phenotype. Both the decrease in CD4$^+$ T-cell proliferation and the increase in pDC numbers in PBMC cultured with HKL are consistent with antigen-specific tolerance induction (Colonna et al, *Nat Immunol* 5:1219-1226, 2004).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Bauer et al, *Allergy* 54(8):894-895, 1999
Bernard et al, *Allergy* 58(12):1285-1292, 2003
Beyer et al, *J Allergy Clin Immunol* 109(4):7070-713, 2002
Bock, *Pediatrics* 79(5):683-688, 1987
Bock et al, *J Allergy Clin Immunol* 107(1):191-193, 2001
Bock and Atkins, *J Allergy Clin Immunol* 83(5):900-904, 1989
Boyle et al, *Am J Clin Nutr* 83(6):1256-1264, 2006
Boyle et al, *Syst Rev*, Oct. 8, 2008 Issue 4, CD006135
Buchanan et al, *J Allergy Clin Immunol* 119(1):199-205, 2007
Chen et al, *Science* 265(5176):1237-1240, 1994
Chung et al, *J Allergy Clin Immunol* 109(1):150-154, 2002
Chung et al, *J Leukoc Biol* 77(6):906-913, 2005
Colonna et al, *Nat Immunol* 5:1219-1226, 2004
Daniel et al, *Allergy* 52(11):1237-1242, 2007
Dunstan et al, *J allergy Clink Immunol* 112:1178-1184, 2003
Enrique et al, *J Allergy Clin Immunol* 116(5):1073-1079, 2005
Frossard et al, *J Allergy Clin Immunol* 114(2):377-382, 2004
Groux et al, *Nature* 389(6652):737-742, 1997
Grundy et al, *J Allergy Clin Immunol* 110(5):784-789, 2002
Gupta et al, *Thorax* 62(1):91-96, 2007
Hamalaninen et al, *Anal Biochem* 299:63-70, 2001
Hourihane et al, *J Allergy Clin Immunol* 100(5):596-600, 1997
Hourihane et al, *Bmj* 316(7140):1271-1275, 1998
Karlsson et al, *J Exp Med* 199 (12):1679-1688, 2004
Kemp et al, *Arch Intern Med* 155(16):1749-1754, 1995
Kerzl et al, *J Allergy Clin Immunol* 119(2):507-508, 2007
Kieser and Friede, *Statistics in Medicine* 26:253-273, 2007
Leung et al, *N Engl J Med* 348(11):986-993, 2003
Matsuzaki and Chin, *Immunology & Cell Biology*, 78:67-73, 2000
Meglio et al, *Allergy* 59(9):980-987, 2004
Mehr et al, *Paediatr Allergy Immunol* 18(5):448-452, 2006
Mernard et al, *J Pediatric Gastroenterology & Nutrition* 43:451-458, 2006
Mullins, *Med J Aust* 186(12):618-621, 2007
Nelson et al, *J Allergy Clin Immunol* 99(6 Pt1):744-751, 1997
Norman, *J Allergy Clin Immunol* 113(6):1013-1023, 2004
Nucera et al, *Dig Dis Sci* 45(3):637-641, 2000
Osborne and Sinn, *Probiotics in infants for prevention of allergic disease and food hypersensitivity* (Review), Cochrane Database *Syst Rev* Art No. CD006474, 2007
Osborne and Sinn, *Probiotics in infants for prevention of allergic disease and food hypersensitivity* (Review), Cochrane Database *Syst Rev* Art No. CD006475, 2007

Patriarca et al, *Aliment Pharmacol Ther* 17(3):459-465, 2003
Perez-Machado et al, *Eur J Immunol* 33(8):2307-2315, 2003
Primeau et al, *Clin Exp Allergy* 30(8):1135-1143, 2000
Pumphrey, *Curr Opin Allergy Cin Immunol* 4(4):285-290, 2004
Rautava et al, *Pediatr Res* 60(2):221-224, 2006
Roberts and Lack, *J Allergy Clin Immunol* 115(6):1291-1296, 2005
Robertson et al, *Med J Aust* 180(6):273-276, 2004
Rolinck-Werninghaus et al, *Allergy* 60(10):1320-1322, 2005
Sampson, *J Allergy Clin Immunol* 107(5):891-896, 2001
Schabussora and Widermann, *Curr Opin Allergy Clin Immunol* 8(6):557-564, 2008
Schmidt-Weber and Blaser, *Springer Semin Immunopathol* 25(3-4):377-390, 2004
Shida et al, *Clin Exp Allergy* 32:563-570, 2002
Sicherer et al, *Pediatrics* 102(1):199-205, 1998
Sicherer et al, *Pediatrics* 105(2):359-362, 2000
Sicherer et al, *J Allergy Clin Immunol* 112(6):1203-1207, 2003
Skolnick et al, *J Allergy Clin Immunol* 107(2):367-374, 2001
Strobel and Mowat, *Curr Opin Allergy Clin Immunol* 6(3):207-213, 2006
Tureanu et al, *J Clin Invest* 111(7):1065-1072, 2003
Vander Leek et al, *J Pediatr* 137(6):749-755, 2000
Wensing et al, *J Allergy Clin Immunol* 110(6):915-920, 2002
Young et al, *Lancet* 343(8906):1127-1130, 1994

What is claimed is:

1. A method for treating food intolerance to peanut allergen in a human subject intolerant to peanut, said method comprising administering sequentially or simultaneously to said human subject a probiotic and peanut allergen in an amount effective to induce tolerance to peanut allergen, wherein the probiotic and peanut allergen are for use in treatment of said subject rather than prophylaxis, are provided in two different formulations, are both administered orally and the probiotic is *Lactobacillus rhamnosus*.

2. The method of claim 1 further comprising administration of a prebiotic.

3. A method for inducing food tolerance to peanut allergen in a human subject with peanut allergy said method comprising administering sequentially or simultaneously to said subject a probiotic and peanut allergen in an amount effective to induce tolerance to peanut allergen, wherein the probiotic and peanut allergen are for use in treatment of said subject rather than prophylaxis, are provided in two different formulations, are both administered orally and the probiotic is *Lactobacillus rhamnosus*.

4. The method of claim 3 further comprising administration of a prebiotic.

* * * * *